US006875583B2

(12) United States Patent
Giberson et al.

(10) Patent No.: US 6,875,583 B2
(45) Date of Patent: Apr. 5, 2005

(54) RAPID MICROWAVE-ASSISTED FIXATION OF FRESH TISSUE

(75) Inventors: Richard T. Giberson, Chico, CA (US); Douglas Edwin Elliott, Oroville, CA (US)

(73) Assignee: Ted Pella, Inc., Redding, CA (US)

( * ) Notice: Subject to any disclaimer, the term of this patent is extended or adjusted under 35 U.S.C. 154(b) by 45 days.

(21) Appl. No.: 10/152,856

(22) Filed: May 22, 2002

(65) Prior Publication Data

US 2002/0177183 A1 Nov. 28, 2002

Related U.S. Application Data

(60) Provisional application No. 60/292,817, filed on May 22, 2001.

(51) Int. Cl.[7] ................................................. G01N 1/30
(52) U.S. Cl. ................ 435/40.5; 435/40.52; 435/173.1; 435/1.1
(58) Field of Search ............................... 435/1.1, 40.5, 435/173.1, 40.52

(56) References Cited

U.S. PATENT DOCUMENTS 4,656,047 A    4/1987  Kok et al.
5,244,787 A    9/1993  Key et al.

OTHER PUBLICATIONS

U.S. Appl. No. 10/128,012, filed Apr. 23, 2002, Giberson et al.
U.S. Appl. No. 60/292,817, filed May 22, 2001, Giberson and Elliott.
Tentative U.S. Appl. No. 10/210,320, filed Aug. 1, 2002, Richard T. Giberson.
Mayers, C.P., 1970, Histological fixation by microwave heating. J. Clin. Pathol. 23:273–275.
Login, G.R., 1978, Microwave Fixation Versus Formalin fixation of Surgical and Autopsy Tissue. American Journal of Medical Technology, 44:435–437.
Burnett, M.G., 1982.The Mechanism of the Formaldehyde Clock Reaction. Journal of Chemcial Education. 59:160–162.
Fox, C.H. et al., 1985. Formaldehyde Fixation. The Journal of Histochemistry and Cytochemistry. 33:845–853.
Boon, M.E. et al., 1986. Microwave–stimulated diffusion for fast processing of tissue: reduced dehydrating, clearing, and impregnating times. Histochemistry, 91:213–220.
Wild, P. et al., 1989. Potency of microwave irradiation during fixation for electron microscopy. Histochemistry, 91:213–220.
Horobin, R.W. and Fleming, L., 1990. 'Trouble–shooting' microwave accelerated procedures in histology and histochemistry: understanding and dealing with artifacts, errors and hazards. Histochemical Journal, 22:371–376.

Kok, L.P. and Boon, M.E., 1990. Microwaves for microscopy. Journal of Microscopy, 158:291–322.
Kok, L.P. and Boon, M.E., 1990. Physics of microwave technology in histochemistry. Histochemical Journal 22:381–388.
Leong, Anthony .S–Y., 1991. Microwave Fixation and Rapid Processing in a Large Throughput Histopathology Laboratory. Pathology 23:271–273.
Kang, Z. et al., 1991. Microwave fixation of rust–infected wheat leaves. Protoplasma, 162:27–37.
Benhamou, N. et al., 1991. Microwave energy fixation of plant tissue: An alternative approach that provides excellent preservation of ultrastructure and antigenicity. Journal of Electron Microscopy Technique, 17:81–94.
Kok, L.P. and Boon, M.E., 1992. Microwave Cookbook for Microscopists—Art and Science of Visualization. Coulomb Press Leydon, The Netherlands, pp. 137–175.
Leong, Anthony S–Y., 1993, Microwave techniques for diagnostic laboratories. SCANNING. 25;88–89.
Hopwood, D., 1993. Microwaves and tissue processing. USA Microscopy & Analysis, Jul. 1993, 1:23–25.
Login, G.R. and Dvorak, A.M., 1993. A review of rapid microwave fixation technology: its expanding niche in morphologic studies. SCANNING, 15:58–66.
Walker, J.F., 1964. Formaldehyde. American Chemical Society Monograph Series. Reinhold Publishing Corp., Chapman & Hall, Ltd., London, pp 52–82.
Helander, K.G., 1999. Formaldehyde Binding in Brain and Kidney: A Kinetic Study of Fixation.. The Journal of Histotechnology, Dec. 1999, 22:No. 4, pp. 317–318.
Leong, Anthony S–Y, 1994. Microwave technology for morphological analysis. Cell Vision 1:278–288.

(Continued)

Primary Examiner—Leon B. Lankford, Jr.
Assistant Examiner—Ruth A. Davis
(74) Attorney, Agent, or Firm—Rick Martin; Patent Law Offices of Rick Martin, P.C.

(57) ABSTRACT

A rapid method of microwave-assisted formalin fixation of tissue that is described as: (a) a two-step process; (b) applicable to large (>5 mm thick) and small (<5 mm thick) tissues; (c) exposure of fresh tissue (i.e. a surgical biopsy) in a formalin solution to continuous microwave irradiation; (d) formalin circulated and cooled to maintain a constant temperature; (e) microwave-assisted formalin fixation performed at a temperature between 4° C. and 40° C.; (f) a temperature probe used to monitor fixative temperature in the cavity (g) after processing via microwave-assisted formalin fixation, the tissue can be processed by microwave methods or in an automatic tissue processor into paraffin for diagnostic evaluation. The two step process consists of a first low power microwave run followed by a second high power microwave run. An alternate embodiment of the present invention employing a one step MW oven process using other selected fixatives (glyoxal, glyoxal based and other aldehyde fixatives, alcohol, acetone, etc.)

16 Claims, 8 Drawing Sheets

OTHER PUBLICATIONS

Boon, M.E. and Kok, L.P., 1994. Microwaves for Immunohistochemistry, Micron., 25:151–170.

Login, G.R. and Dvorak, A.M., 1994. methods of microwave fixation for microscopy: A review of research and clinical applications: 1970–1992, Prog. 27:1–127.

Giberson, R.T. and Demaree, R.S. Jr., 1995. Microwave fixation: Understanding the variables to achieve rapid reproducible results. Microscopy Research and Technique 32:246–254.

Kok, L.P. and Boon, M.E., 1996. New developments of Microwave Technology in Pathology: Combining Vacuum with Microwave Irradiation. Cell Vision 3:224.

Giberson, R.T. et al., 1997. Four–hour processing of clinical/diagnostic specimens for electron microscopy. J Vet Diagn Invest. 9:61–67.

Majetich, J. and Wheless, K., 1997. Microwave heating in organic chemistry—An update. In: Microwave heating in organic chemistry—Fundamentals, Sample Preparation, and Applications, H. M. Kingston and S. J. Haswell, eds. American Chemical Society, Washington, DC, p. 481–482.

Kok, L.P. and Boon,M.E., 1997. Microwave Methods for Sample Preparation in Pathology. In: Microwave–Enhanced Chemistry—Fundamentals, Sample Preparation, and Applications, H. M. Kingston and S.J. Haswell, eds. American Chemical Society, Washington, DC, pp. 641–654.

Gamble, M., 1998. A guide to automating the histology laboratory. Laboratory Medicine 29:497–501.

Crowder, C.H. and Giberson, R., 1998. Microwave processing: clinical laboratory methods for paraffin, special stains, decalcification and electron microscopy. National Society for Histotechnology Annual Meeting, Salt Lake City, UT. Workshop #57, Sep. 14, 1998; abstract only.

Battifora, H., 1999. Quality assurance issues in immunohistochemistry. The Journal of Histotechnology. 22:169–175.

James, J.D. and Hauer–Jensen, M., 1999. Effects of Fixative and Fixation Time for Quantitative computerized image analysis of Immunohistochemical Staining. The Journal of Histotechnology 22:109–111, Jun. 1999.

Giberson, R.T. and Elliott, D.E., 2001. Microwave–assisted Formalin Fixation of Fresh Tissue: A Comparative Study. In: Microwave Techniques and Protocols, Giberson, R.T. and Demaree, R.S., Jr., eds. Humana Press, Totowa, NJ, pp 191–208.

http://www.ebsciences.com/microwave/fixative.htm,2002. Procedure: Microwave Stimulated Fixation with Preserve.

http://my.net–link.net/~anatech/www/anatech/prefer99.html, 2002. Anatech Ltd.'s Prefer.

New Tissue Fixation Method for Gytochemistry Using Microwave Irradiation . Authors: Vince Mizuhira, Mitsuru Notoya and Hiroshi Hasegawa. Acta Histochemica et Cytochemica, vol. 23, No. 4, 1990.

Microwave applications on small insect brain tissue irradiated in a water–perfused cooling–jacket for temperature control. Author: Hans M. Smid. Journal of Neuroscience Methods; Department of Entomology, Wageningen Agricultural University, Binnenhaven 7, 6709 PD Wageningen, The Netherlands. Accepted Aug. 18, 1994.

RAPID MICROWAVE-ASSISTED FIXATION OF FRESH TISSUE

CROSS-REFERENCE TO RELATED APPLICATION

This application is a non-provisional application claiming the benefits of provisional application No. 60/292,817 filed May 22, 2001.

FIELD OF THE INVENTION

This application relates to the fields of clinical and research pathology and particularly to those tissue biopsies that are processed into paraffin for subsequent diagnostic evaluation. More specifically, the present invention relates to a method of fixation of tissue samples using formalin with a two step microwave (MW) irradiation and a MW oven with continuous power output.

BACKGROUND OF THE INVENTION

Over the last two decades there has been a growing interest in accelerating the processing steps of tissue biopsies that are embedded in paraffin for diagnostic evaluation. Clinical and research analysis of tissue samples is an ongoing science. The major forces driving reduced processing times are improved patient care and the control of rising medical costs. Equipment has been on the market for a number of years to reduce all the processing steps, to include slide preparation, of a surgical biopsy except for formalin fixation. It is well known in the art that formalin remains the most popular fixative for light microscopy and pathology. It is the fixative that defines the morphological basis for diagnostic pathology.

Tissue samples are routinely placed in plastic tissue processing cassettes, after grossing, for fixation in formalin. Grossing is the act of taking a large tissue sample and cutting it down into smaller tissue sizes.

It is well know in the art that fixation is the single most important step in processing of tissue for clinical and research pathology because:

(1) It stabilizes tissue proteins and other cellular constituents to withstand the rigors of processing; and
(2) Without adequate fixation the quality of results used for diagnostic evaluation are subject to compromise.

Ironically, the least controlled step in tissue processing for samples derived from clinical or research pathology is fixation. As is well known in the art, processing—after fixation—is done by either automatic tissue processors or MW-assisted processing. Either process cycles the tissue cassettes through dehydration (usually a graded series of ethanol), an intermedium (usually xylene, isopropanol or xylene substitutes), and molten paraffin in a controlled environment.

The only piece of equipment, known to the inventors, that has been exploited to optimize and accelerate the fixation step is the MW oven. Formalin, used as a fixative, is typically diluted to a concentration of 10% and buffered to maintain a desired Ph. Formalin is a 37–40% solution of formaldehyde. 10% NBF (neutral buffered formalin) is a buffered 1:10 dilution of formalin concentrate (approximately 4% formaldehyde solution) and approximately 1% methanol. As a fixative, formalin is known for its ability to quickly penetrate tissue, but it is also known in the art that, once in the tissue, chemical stabilization (fixing and/or cross-linking proteins) of the tissue takes places slowly. Formalin fixation is generally considered, by those knowledgeable in the art, to take at least 24 hours or longer for tissue biopsies and requires 4–6 hours just to penetrate tissue blocks up to 5 mm thick.

As known in today's art, MW methods to optimize and/or accelerate the fixation process have been subdivided into 5 classifications:

1) MW stabilization—tissue placed in a non-fixative solution, usually normal saline, and heated to temperatures between 45 and 70° C. in the MW—it can also apply to tissues not placed in a solution and stabilized by MW's alone;
2) MW-assisted chemical fixation—tissue placed in a fixative solution and irradiated—a process, to the inventors knowledge, that is only used for tissues being processed for electron microscopy;
3) MW-assisted chemical fixation followed by immersion of tissue in fixative outside the MW;
4) Chemical fixation of the tissue outside the MW for minutes or hours followed by MW-assisted chemical fixation; and
5) MW irradiation used in combination with freeze fixation.

MW stabilization, #1 above, produces rapid results (under 10 minutes) but suffers from a number of disadvantages unique to the process. Other than a substitute for the use of formalin there seems to be little interest in the process in the United States. MW-assisted chemical fixation, #2 above, has worked well with a number of aldehyde fixatives and fixative combinations for samples less than 1 $mm^3$ in size and almost always destined for electron microscopic evaluation. Other than endoscopic or needle biopsies, which conform to the 1 $mm^3$ size parameters, this method has not been described as a means of processing for clinical or research pathology. MW-assisted chemical fixation followed by immersion, #3 above, in the fixative outside the MW is a method used to circumvent the reported problems inherent with MW-assisted chemical fixation. Chemical fixation of the tissue for a period outside the MW, #4 above, is primarily a method used in clinical and research pathology to overcome the problems associated with the fixation of fresh tissue in formalin (see below). MW irradiation used in combination with freeze fixation, #5 above, is an established method for improving the morphology of cryostat sections.

MW-assisted formalin fixation of fresh tissue has been attempted without success. This lack of success is attributed to the mechanism of formalin fixation, as described in literature of the present art.

The following is the proposed mechanism steps of formalin fixation:

1) The diffusion of methylene glycol into the tissue—formaldehyde fixative solutions contain little formaldehyde, instead the primary chemical reagent is methylene glycol formed by the reaction of formaldehyde gas and water;
2) The formation of formaldehyde, the fixation component, by the dehydration reaction of methylene glycol in the tissue; and
3) Binding of formaldehyde to the proteins by chemical cross-linking of the formaldehyde to tissue proteins and other cellular components.

When MW or other heating methods heat formalin, it is thought that steps 2 and 3, as outlined above, take place. So for fresh tissue, the heating (MW or other) results in the formation of formaldehyde wherever methylene glycol is present in or around the tissue. The resulting formaldehyde cross-links with the proteins in the tissue that creates a dense matrix, stopping further penetration of the formalin into the tissue. It has been demonstrated in a model system that aldehyde cross-linking takes place when the system is exposed to MW irradiation. It has also been demonstrated that dehydration reactions take place under the influence of MW heating. From the experience of the inventors, the penetration of formalin in fresh tissue is limited to approximately the outer 0.75 mm of the tissue when the MW is used at full power. During a workshop at the National Society for Histotechnology meeting (1998, Salt Lake City, Utah) the inventors demonstrated for the first time that variable power control and intermittent MW energy could be used to fix fresh tissue in formalin with MW irradiation.

The primary variable responsible for MW-accelerated fixation in the literature is attributed to MW induced heating of either a fixative or solution. The present invention provides an alternative that has not been previously described in the literature. This alternative of the present invention expands on previous knowledge by:

1) Using continuous MW energy initially at a low power output of the magnetron (typically at or below 250W);
2) Changing the continuous power output of the magnetron after approximately 75% of the total time has elapsed to a higher level of continuous power at or above 450W;
3) (1) and (2) are performed while circulating and cooling the formalin so that MW heating is held within in a narrow range (±0.5° C.);
4) (1) and (2) are performed while controlling formalin temperatures during MW irradiation between 4° C. and 40° C.; and
5) Proposing a plausible method by which this process takes place.

SUMMARY OF THE INVENTION

The main aspect of the present invention is to provide an improved method described as a rapid, controlled process for MW-assisted formalin fixation of fresh tissue with negligible MW heating of the formalin and tissue and continuous MW energy.

Another aspect of the present invention is to provide a method for MW-assisted chemical fixation of fresh tissue that is dependent on MW power as measured by continuous power output of the magnetron (even when changing wattage levels) and independent of temperature.

Another aspect of the present invention is to provide for continuous circulation and cooling of the fixative outside of the MW oven using formalin, the preferred embodiment, as a fixative.

Still another aspect of the present invention is to maintain the formalin at a set temperature between 4° C. and 40° C. while controlling the set temperature within ±0.5° C.

Still another aspect of the present invention is to employ a first step whereby a MW oven is set at a fixed wattage (at or below 250W) and at a specific time period to facilitate the diffusion of methylene glycol into the tissue without conversion of the methylene glycol into the fixative agent.

Yet another aspect of the present invention is to employ a second step whereas the MW oven fixed wattage is changed to a higher level (at or above 450W) for a fixed time to promote the chemical conversion of the methylene glycol into formaldehyde, the fixative agent, to promote the uniform chemical fixation of the tissue by the formaldehyde.

Another aspect of the present invention is to provide a methodology whereby all processing parameters are controlled. Such parameters include the amount of MW irradiation, wattage, temperature, time, etc.

Another aspect of the present invention, an alternate embodiment, is to use a one step process when fixatives other than formalin are used. These fixative would include, but not be limited to, other aldehydes, alcohol, acetone, Prefer™, Preserve™, GlyoFixx, SafeFix II, etc.

Another aspect of the present invention is to increase productivity by reducing tissue sample turnaround time while producing excellent processing results.

Other aspects of this invention will appear from the following description and appended claims, reference being made to the accompanying drawings forming a part of this specification wherein like reference characters designate corresponding parts in the several views.

It is desirable that a tissue sample fixation technique be simple, rapid, reproducible and able to be implemented with currently-existing MW technology.

The process of the present invention demonstrates that:

A. MW-assisted formalin fixation of fresh tissue is not a heat dependent process;
B. MW-assisted formalin fixation of fresh tissue is dependent on the continuous power output of the MW oven magnetron;
C. A low (at or below 250W) continuous power from the MW oven magnetron is required for diffusion of the methylene glycol to take place in the tissue;
D. A higher (at or above 450W) continuous power from the MW oven magnetron is required to form formaldehyde from methylene glycol;
E. The formaldehyde cross-links to the tissue proteins and chemically stabilizes the tissue to withstand the rigors of further required processing;
F. Constant temperature control and continuous circulation of the formalin optimizes the process; and
G. The quality of preservation of the MW-assisted formalin-fixed tissues as proposed in this patent is indistinguishable from tissues fixed 24 hours by routine unimproved methods.

Although the preferred embodiment of the present invention relates to formalin as a fixative, it should be noted that the alternate embodiment of the present invention is described with the use of other fixatives, aldehydes, alcohol, acetone, Prefer™, Preserve™, GlyoFixx, SafeFix II, etc. The alternate embodiment differs primarily in one major aspect, that of using a single step microwave process.

DETAILED DESCRIPTION OF INVENTION

The present invention provides a new and unique approach to the problem of the fixation of fresh tissue in formalin. The method of the present invention employs previously untried variables in MW processing techniques either for fixation or other processing protocols. The mechanism of MW irradiation and fixation of fresh tissues in formalin can be evaluated based on existing knowledge in the art. The process of the present invention applies to both mineralized and non-mineralized tissue.

The method of the preferred embodiment of the present invention is based on formalin. Formalin is the most commonly used fixative in clinical and research pathology today, and therefore presents the ability for improvement in fixation quality, speed and reproducibility. This improvement can be directly applied to the problem of time savings and cost control in tissue processing for clinical and research pathology.

Although the method of the present invention has not been applied to every tissue type seen in clinical and research pathology, it is a method that has worked in every tissue type tried by the inventors to date. It is therefore believed that the methodology used by the present invention is applicable to the broad spectrum of tissues that are encountered in everyday clinical and research pathology. The methodology of the present invention has been applied to animal tissues and evaluated by qualified pathologists. In all evaluations MW-assisted formalin fixed tissues have been chosen as equals to tissues fixed for 24 hours in formalin by routine methods. MW-assisted formalin-fixed tissues have been processed at time ranges between 4–8 minutes (for 1 mm thick samples) to 90 minutes (for greater than 5 mm thick samples).

The ability to control and change the continuous power output of a microwave's magnetron during processing is the critical variable. Previous research and MW-assisted methods of processing have been dependent on the existing MW technology. Continuous power, variable wattage MW oven technology for tissue processing is readily available (i.e. Ted Pella, Inc. Redding, Calif.). This technology made it possible to explore variables other than MW heating. The design of a variable wattage MW, along with an external heating/cooling recirculation device, made it possible to control the temperature of the formalin external to the MW cavity and at the same time continuously monitor the temperature of the formalin within the MW cavity. An RS232 port can be used to transmit temperature and time data to software, making it possible for a PC to capture a temperature and time profile of any MW processing protocol. A temperature probe, for use in the MW cavity, is used to monitor and control preset temperature maximums of the processing solution. A load cooling device is used in tissue processing applications, which recirculates and cools solutions outside the MW cavity. The MW magnetron provides continuous power even when wattage is changed from one level to another. Continuous power is defined herein as being within the design of the MW oven. That is, power may be supplied within the design as constant on or via a duty cycle.

The circulation and cooling of formalin outside the MW cavity creates the following conditions inside the MW cavity:

1) A constant formalin temperature is maintained between 4–40° C. (±0.5° C.) inside the MW cavity;
2) A constant temperature is maintained throughout the entire MW-assisted formalin fixation process;
3) The magnetron of the MW is on continuously during the fixation;
4) MW heating of the fixative is verified and held within ±0.5° C. of a desired temperature between 4° C. and 40° C. as measured by the temperature probe within the cavity;
5) Fixation of fresh tissue in formalin is accomplished at all tested temperatures between 4° C. and 40° C.;
6) The time interval required for fixation at 40° C. was used for all lower temperature runs;
7) Low power is employed for approximately the first 75% of the time interval and higher power for the remaining 25%;
8) The thickest tissues processed as a group were <5 mm thick and required approximately 60 minutes at 250W and approximately 15 minutes at 450W;
9) Tissues that were 1 mm thick required approximately 4 minutes at 250W and approximately 2 minutes at 450W; and
10) The temperature probe in the MW cavity used to monitor formalin temperatures and adjust the external cooling rate showed a constant temperature within ±0.5° C. of the processing temperature chosen between 4° C. and 40° C.

The present invention employs two distinct process steps that involve separate MW wattage and time settings as previously described. The first step of the process involves a MW oven at a fixed wattage (at or below 250W) and for a specific time period that acts to facilitate the diffusion of methylene glycol into the tissue without conversion of the methylene glycol into the fixative agent. The second step involves setting the MW oven at a second fixed wattage (changed to a higher level at or above 450W) for a second fixed time in order to promote the chemical conversion of methylene glycol into formaldehyde, the fixative agent, to promote the uniform chemical fixation of the tissue by the formaldehyde. It should be noted that in using a typical MW oven with a programmable step memory, each of the above steps could be preset into memory by the user, thereby requiring no user interaction once the process has started. Thus, the aforementioned steps one and two could be integrated into one programmable step.

The 10% NBF discussed earlier is approximately 96% water. The remaining 4% chemical constituent is approximately 99.90% methylene glycol and 0.1% formaldehyde, which is the active fixative component. With the present invention, the use of a MW at the first low wattage step acts to completely diffuse the methylene glycol into the tissue without shifting the chemical equilibrium of the solution. With the second higher wattage step of the process, a shift in chemical equilibrium takes place whereby a dehydration reaction is set up, which in turn, forms more formaldehyde from methylene glycol. The formaldehyde then cross-links to the tissue proteins to complete the fixation, which chemically stabilizes the tissue to withstand the rigors of further required processing.

An alternate embodiment of the present invention employs use of other fixative solutions such as aldehydes, alcohol, acetone, Prefer™, Preserve™, GlyoFixx, SafeFix II, etc. When these other fixatives are employed the MW wattage is set at one wattage (50 w to 900 w) depending on tissue specimen for a specific time period and a constant temperature is maintained between 4–40° C. (±0.5° C.) inside the MW cavity as the fixative solution continuously recirculates via an external heating and cooling device.

EXAMPLES

Fixation of fresh tissue in formalin cannot proceed without control of continuous power output by the MW magnetron. If the fixation of fresh tissue in formalin is attempted without the ability to control the continuous power output of the magnetron of the MW, then the periphery of the tissue is the only region that will be chemically fixed. Continuous MW irradiation at or below 250W promotes the diffusion of formalin into tissues without the conversion of methylene glycol into formaldehyde. The thickness of the tissue being processed determines the time interval required for MW irradiation at power levels at or below 250W to achieve diffusion of methylene glycol into the tissue. For tissue specimens <5 mm thick, it has been found that this first time period does not typically exceed 60 minutes.

In the second step of the process, the continuous power output of the magnetron is then changed to an output level at or above 450W to facilitate the conversion of methylene glycol to formaldehyde and promote the complete chemical fixation (cross-linking of formaldehyde with tissue proteins)

of the tissue by formaldehyde. It is maintained by the present invention that high wattage output of the magnetron facilitates the conversion of methylene glycol to formaldehyde and the cross-linking of the formaldehye to tissue proteins.

When similar tissue samples were processed only at continuous power outputs of the magnetron below 250W, chemical fixation by formalin could not be demonstrated. When the same tissue samples were processed only at continuous power outputs of the magnetron above 450W, only the periphery of the tissue was fixed. These results indicate that MW heating is not a major variable between 4° C. and 40° C. and that MW magnetron power output is the most important variable. Continuous power output of the MW magnetron also eliminates variations in the amount of MW irradiation to which the tissues and formalin are exposed. Temperature control derived from a temperature probe within the MW cavity will cycle the MW magnetron to maintain a constant and controlled temperature. The amount of MW irradiation during any processing run will vary as a result.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF DRAWINGS

Figure 1:
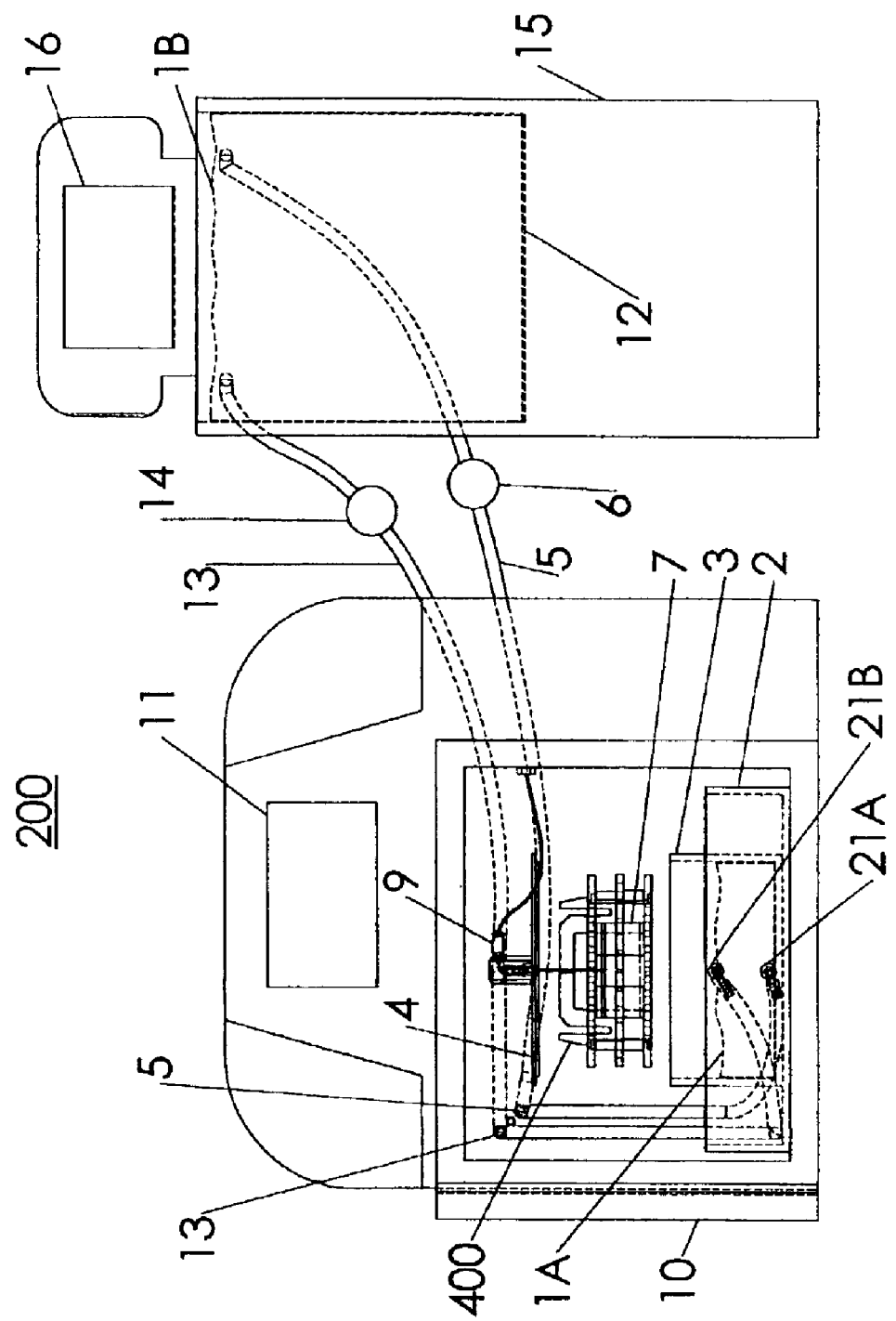
FIG. 1 is a frontal view of the decalcification and fixation apparatus of the present invention.

FIG. 1 is a frontal view of the fixation system apparatus 200 used in the methodology of the present invention. Recirculation device 15 is capable of heating or cooling formalin fixative 1A, 1B via a primary built-in temperature-monitoring device. Inlet tubing 5 and outlet tubing 13 are connected to recirculation device 15 to move formalin fixative 1A, 1B for cooling or heating. The portion of formalin fixative 1B in recirculation device 15 is heated or cooled as it is pumped into tissue processing bath 3 where a portion of formalin fixative 1A resides within the recirculation loop. Recirculation device 15 has a duplex pump and can act as a push/pull device as the formalin fixative is heated or cooled. Recirculation device 15 should be specified to be capable of maintaining the formalin fixative at temperatures to within +/−0.5° C. at 20° when 500 w is being dissipated by MW oven 10. Recirculation device control panel 16 has basic control keys, such as power on/off, temperature setting, temperature display, etc. Recirculation device 15 contains an internal fixative bath 12 and the primary fixative temperature is controlled by recirculation device 15 within its internal fixative bath 12 by the combination of heating and cooling as required. Anti siphon devices 6, 14 help insure that proper solution levels are maintained within tissue processing bath 3. Tubing 5, 13 are connected through an entry point in the rear of MW oven 10 and enter tissue processing bath 3 to form a closed loop system for recirculation. Tubing 5, 13 are capped with inlet fitting 21A and outlet fitting 21B within tissue processing bath 3. Tissue processing bath 3 is an open container, which is fits into overfill safety container 2. Overfill safety container 2 insures any excess reagent is contained without spillage. Tissue samples are prepared and placed on standard histology cassettes 7, which are in turn placed into cassette holder 400. Cassette holder 400 is then placed inside tissue processing bath 3 and thus into and submersed under formalin fixative 1A.

Tissue processing container lid 4 fits snuggly over tissue processing bath 3. Tissue processing lid has one hole in its top, which receives temperature probe 9 that sits within tissue processing bath 3 and acts as a secondary temperature control (in case of a failure in the temperature control portion of recirculation device 15) for temperature monitoring and recording of the formalin fixative 1A temperature. Output from temperature probe 9 can also be monitored by a computer via a RS232 port for temperature data collection. The user prior to starting each step of the fixation process inputs settings on the MW oven control panel 11. Control keys such as power on/off, power settings, start, and reset are inputted.

Figure 1A:
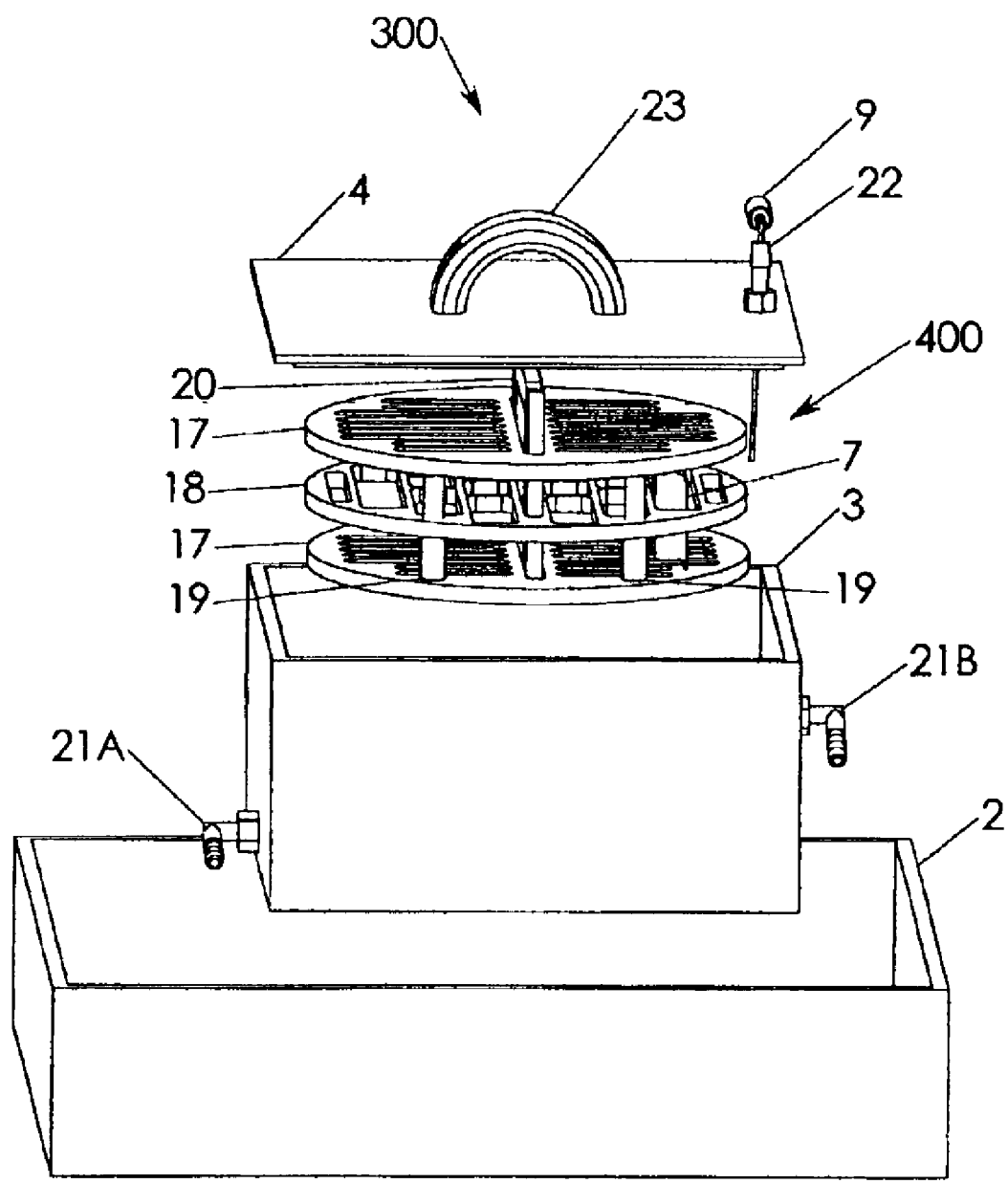
FIG. 1A is an expanded frontal perspective view of the overfill safety container, tissue processing bath and cassette holder.

FIG. 1A is an expanded frontal perspective view 300 of components within the MW oven consisting of overfill safety container 2, tissue processing bath 3 and cassette holder assembly 400. Tissue processing bath 3 fits into overfill safety container 2 and has inlet-fitting 21A attached to its lower side and outlet-fitting 21B attached to its upper side. Outlet-filling 21B maintains the proper fixative solution level within tissue processing bath 3. Cassette holder assembly 400 is made up of cassette holder top and bottom tray 17, which are identical in manufacture, cassette holder center tray 18, cassette holder posts 19 and cassette holder handle 20. Standard histology cassette(s) 7 are held in place within cassette holder assembly 400 during the fixation processing. Tissue processing container lid 4 has tissue processing container lid handle 23 affixed to its top and straight thru fitting 22 to accommodate temperature probe 9 which sits within tissue processing bath 3.

Figure 1B:
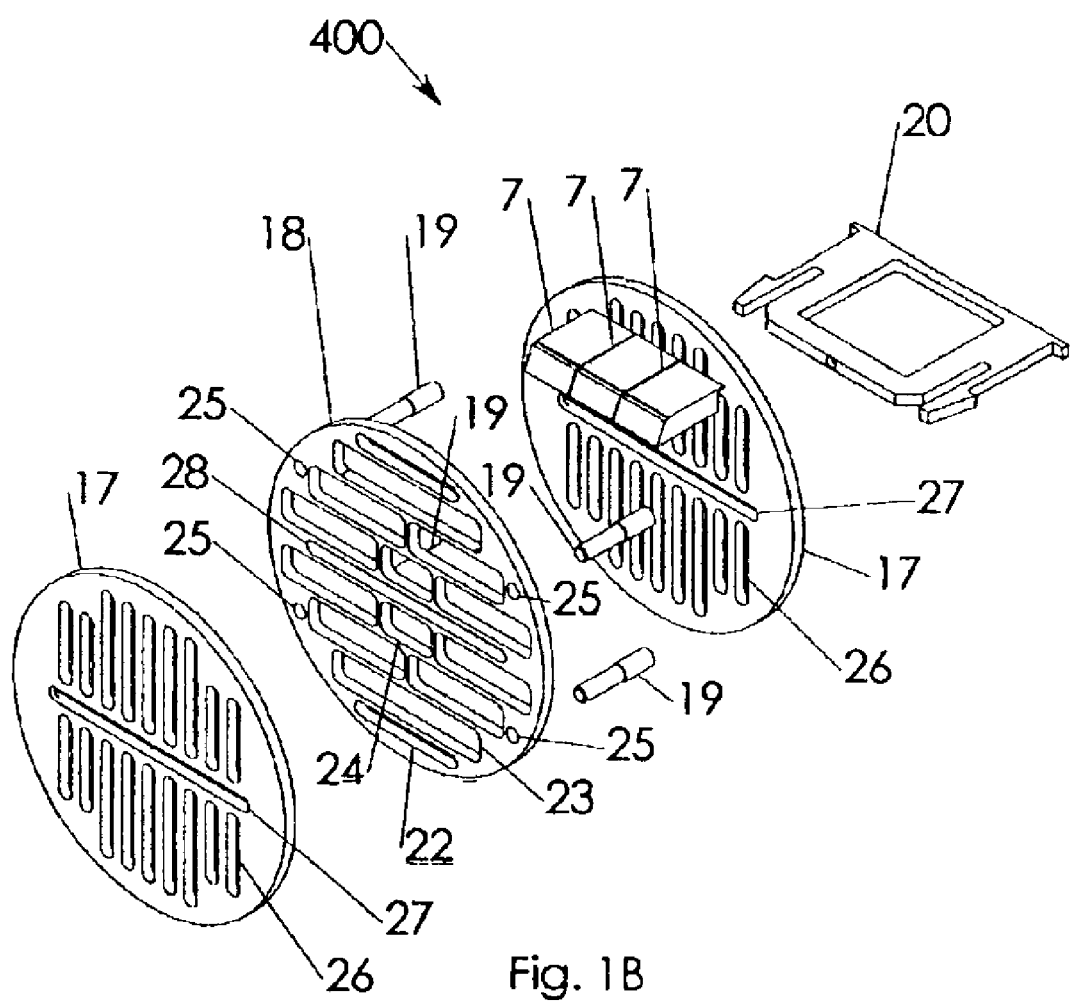
FIG. 1B is an expanded breakaway perspective view of the cassette holder shown in FIG. 1A above.

FIG. 1B is a further expanded breakaway perspective view of cassette holder assembly 400 showing top tray and bottom tray 17, which are identical in manufacture, cassette holder center tray 18, cassette holder posts 19 and cassette holder handle 20. Standard histology cassette(s) 7 are shown held in place within cassette holder assembly 400. Cassette holder handle 20 fits through the entire cassette holder assembly 400 and begins assembly at the bottom of cassette holder assembly 400. Cassette holder handle 20 fits through bottom tray slot 27, then through center tray slot 28, and finally through top tray slot 27 at which point it would snap into place with the top of cassette holder handle 20 protruding for handling and acts to hold the entire cassette holder assembly 400 in place. Center tray 18 has various size retention holes. A three-wide hole 23, a two-wide hole 22, and a one-wide hole 24 can accommodate various histology cassette 7 widths in some cases (only one width shown) or multiple histology cassettes. For example a three-wide hole 23 can accommodate six single-wide histology cassettes (not shown) or three double-wide histology cassettes as shown. Histology cassette(s) 7 can be designed in single- or double-wide widths as needed to accommodate different tissue sample sizes. Center tray 18 has four holder post acceptance holes 25 for inserting holder posts 19. Holder posts 19 function as a height standoff to separate bottom tray 17, center tray 18, and top tray 17. Top and bottom tray 17 have slotted holes 26 of various lengths to accommodate reagent pass through during processing. It should be noted that although only one cassette holder assembly design is shown, other designs are inferred to include accommodation of various other size cassettes such as a thicker cassette holder design which would need a thicker (wider) acceptance hole.

Figure 1C:
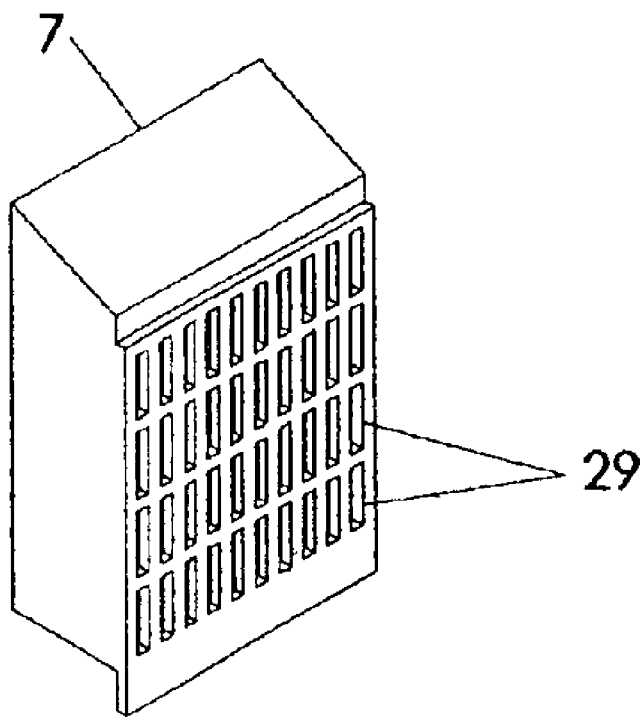
FIG. 1C is a frontal perspective view of standard histology cassette.

FIG. 1C is a frontal perspective view of standard histology cassette 7. Standard histology cassette(s) 7 are placed within cassette holder assembly 400 (see FIG. 1B). Each histology cassette 7 contains a multiple of fluid pass through holes 29 to insure proper circulation of reagent around the tissue specimen (see FIG. 1D) during processing.

Figure 1D:
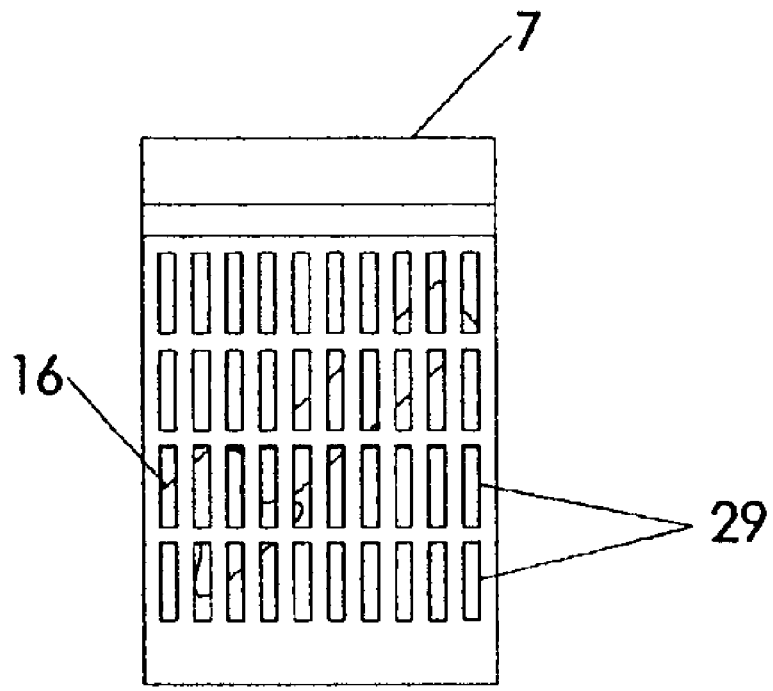
FIG. 1D is a frontal view of standard histology cassette showing an internal tissue sample.

FIG. 1D is a frontal view of standard histology cassette 7 with fluid pass through holes 29 showing internal tissue sample 16, which is held in place by cassette 7 during the decalcification/fixation process.

Figure 2A:
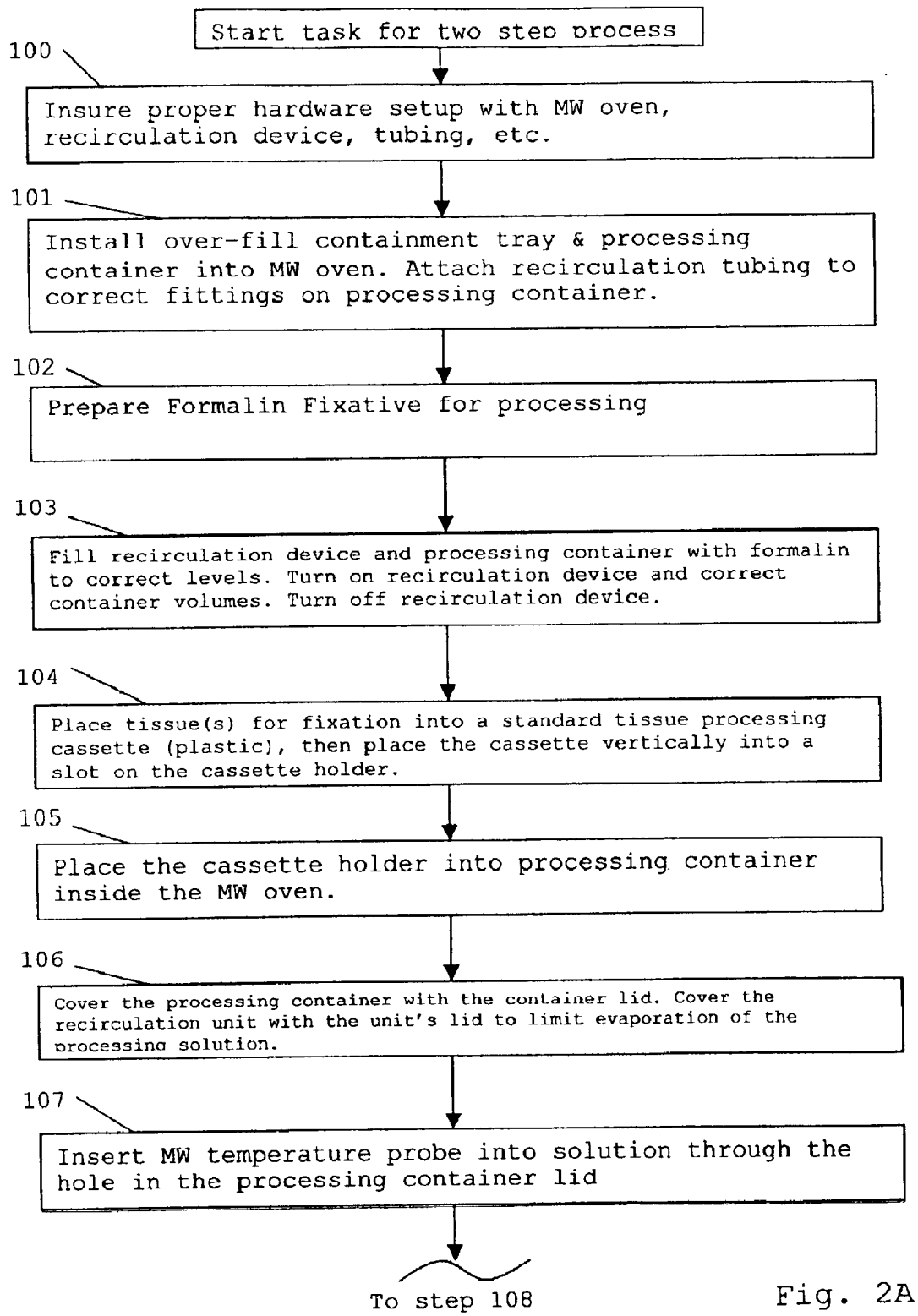
FIGS. 2A, 2B are a flow chart depicting the process steps utilized in the methodology of the preferred embodiment of the present invention.
Figure 2B:
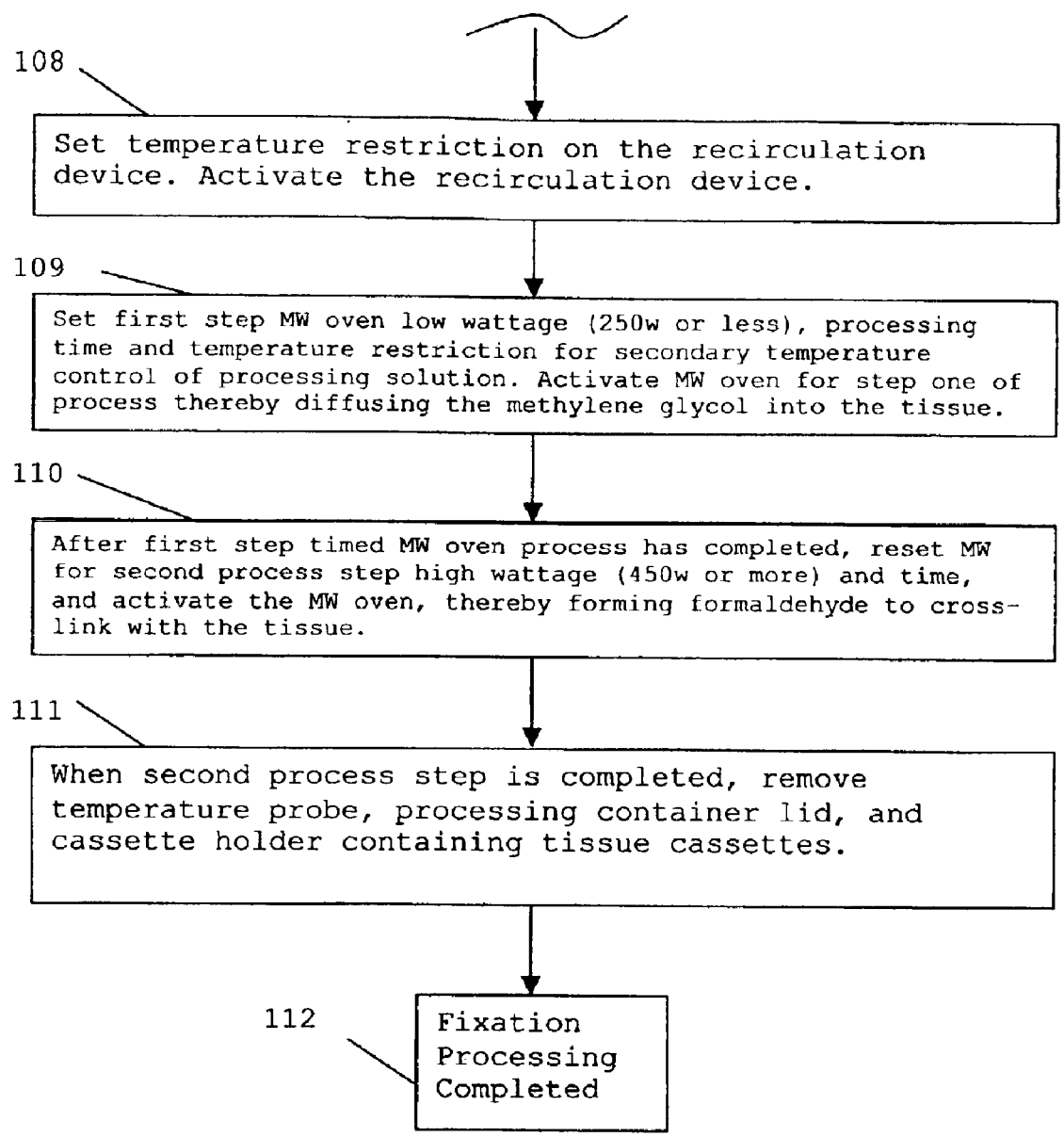

FIGS. 2A, 2B are a flow chart depicting the process steps utilized in the methodology of the present invention. To start the process (FIG. 2A), the first step 100 is to insure proper hardware setup is in place including the MW oven, the recirculation device, tubing attachments, etc. as shown in FIG. 1 above. In step 101, the hardware install is continued with the install of the over-fill containment safety tray and processing container into the MW oven, and attachment of the recirculation tubing to the correct fittings on the processing container. The next step 102 is the preparation of the formalin fixative for filling the processing containers as previously discussed. Next 103 the user will fill the recirculation device and processing container with reagent to the correct levels, turn on the recirculation device and correct the container volumes, then the user would turn off the recirculation device. The process then follows with step 104 in which the tissue sample(s) is placed into a standard tissue processing cassette (plastic material) and then the cassette is placed into the slot of the cassette holder in a vertical position. In the next step 105, the cassette holder is placed into the processing container inside the MW oven. Step 106 consists of covering the processing container with the container lid, covering the recirculation unit with the unit's lid. The lids act to limit any evaporation of the fixative solution. The temperature probe is then inserted into the processing container through the hole in the processing container lid, step 107. Continuing on to FIG. 2B, the next step 108 is to set the temperature restriction on the recirculation device and then to active the recirculation device. Then, in process step one 109, initiating the first step of the process, the MW oven wattage, processing time and temperature restriction for the secondary temperature control of the processing solution is set, followed by activating the MW oven. This first step 109 acts to facilitate the diffusion of methylene glycol completely into the tissue without conversion of the methylene glycol into the fixative agent. After the first process step 109 timed MW oven process is complete, the second process step 110 follows wherein the user resets the MW process time and wattage and re-activates the MW oven. This second process step 110 involves setting the MW oven at a second fixed wattage (changed to a higher level at or above 450W) and a second fixed time and then activating the MW oven. This second process step 110 promotes the chemical conversion of methylene glycol into formaldehyde, the fixative agent, to promote the uniform chemical fixation of the tissue by the formaldehyde. In step 111 the user removes the temperature probe from the lid of the processing container, removes the processing container lid itself, and then removes the cassette holder from the processing tray. The cassette holder contains the tissue cassettes. At this point the process of fixation with formalin is ended 112.

Figure 3A:
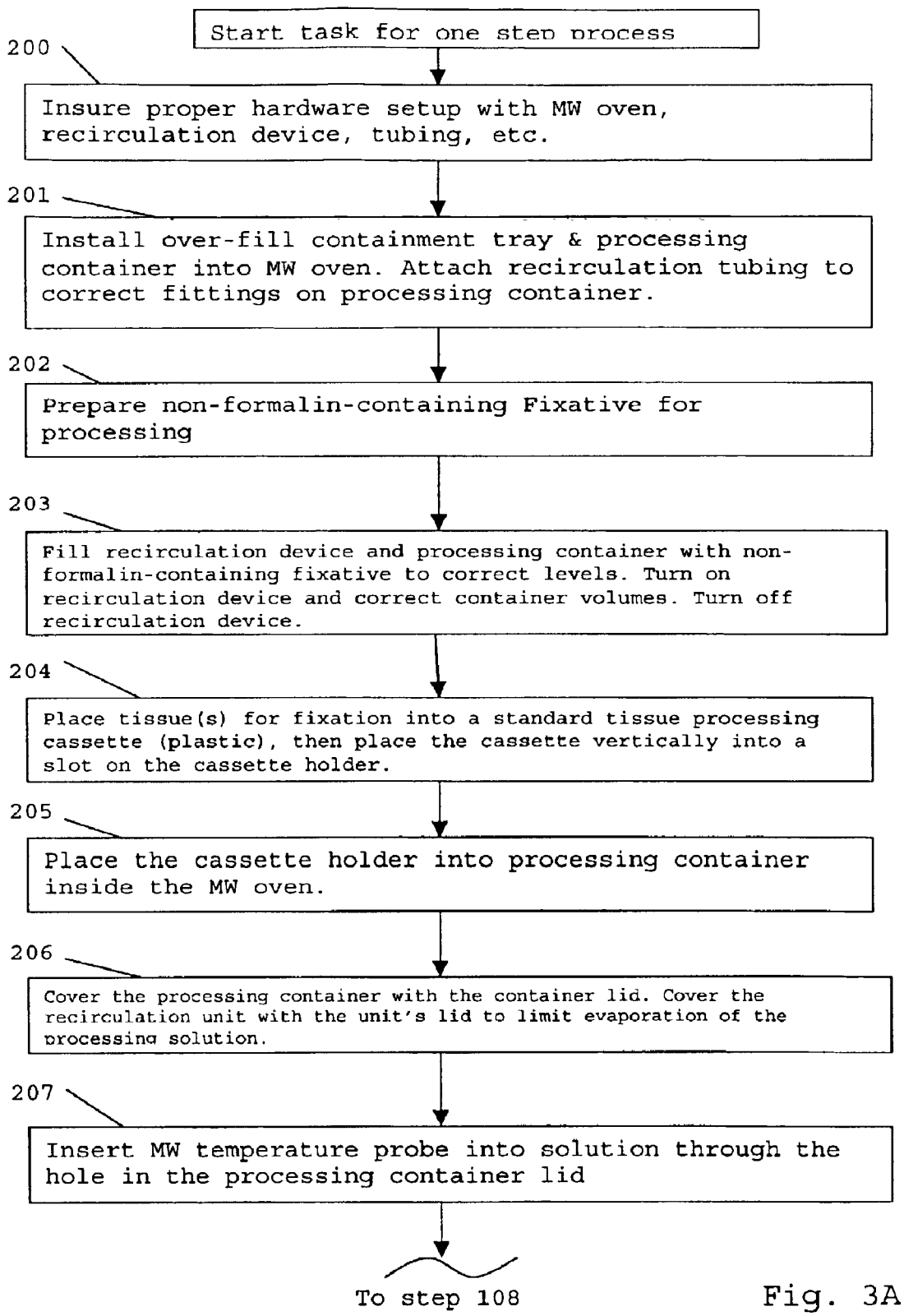
FIGS. 3A, 3B are a flow chart depicting the process steps utilized in the methodology of the alternate embodiment of the present invention.
Figure 3B:
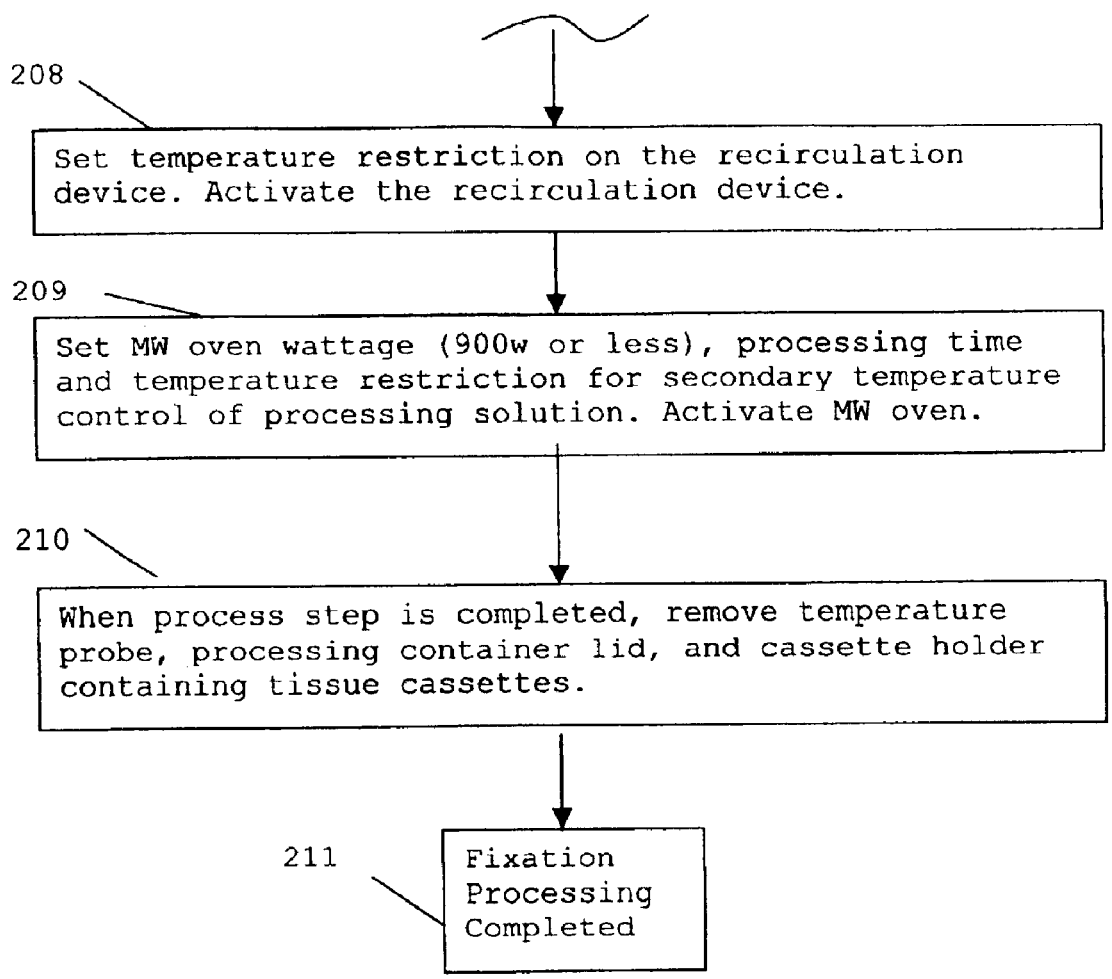

FIGS. 3A, 3B are a flow chart depicting the process steps utilized in the methodology of the alternate embodiment of the present invention which employs use of other fixative solutions such as aldehydes, alcohol, acetone, Prefer™, Preserve™, GlyoFixx, SafeFix II, etc. Steps 200 through 208 are the same as steps 100 through 108 as previously described. In step 209 the MW wattage is set at a predetermined level dependent on the tissue type and size. The process time and temperature control of the processing solution are set and the MW oven is activated. In step 210 the temperature probe, processing container lid and cassette holder are remove. The process is then completed (step 211) and fixation is complete.

Although the present invention has been described with reference to preferred embodiments, numerous modifications and variations can be made and still the result will come within the scope of the invention. No limitation with respect to the specific embodiments disclosed herein is intended or should be inferred.

We claim:

1. A method to fixate a tissue specimen, said method comprising the steps of:
   suspending the tissue specimen in a circulating fluid stream of a formalin based solution;
   during suspending, first irradiating the specimen with a low power microwave radiation for a first set time; and
   during suspending, then irradiating the specimen with a high power microwave radiation for a second set time.
2. The method of claim of claim 1, wherein the low power is less than about 250 watts.
3. The method of claim 1, wherein the high power is more than about 450 watts.
4. The method of claim 1 further comprising the step of selecting the fluid to be formalin.
5. The method of claim 1 further comprising the step of controlling a fluid depth around the tissue specimen to fully immerse the tissue specimen.
6. The method of claim 3 further comprising the step of controlling the fluid temperature in the range of about 4° C. to 40° C., wherein a cooling effect of the fluid prevents the microwave radiation from heating the specimen beyond the range of about 4° C. to 40° C.
7. The method of claim 6 further comprising the step of setting the first set time in the range of about 2–90 minutes, and setting the second set time in the range of about 2–40 minutes.
8. The method of claim 1 further comprising the step of ceasing the irradiating for a period between the first set time and the second set time.
9. A method of fixation comprising the steps of:
   placing a specimen in a solution of formalin within a microwave oven;
   circulating the formalin solution about the specimen;
   maintaining a temperature control from about 4° C.–40° C.;
   first operating the microwave oven in the range of about 250 watts or less power for a first preset time during circulating the formalin solution, thereby promoting a diffusion of formalin into the specimen without converting methylene glycol into formaldehyde within the formalin solution; and
   then operating the microwave oven wattage to a second wattage of about 450 watts or more of power for a second preset time during circulating the formalin solution, thereby promoting the chemical conversion of methylene glycol into formaldehyde and forming a uniform chemical fixation of the tissue.

10. The method of claim 9 further comprising the step of ceasing the operating of the microwave oven between the first preset time and the second preset time.

11. The method of claim 1, wherein the low power microwave radiation is continuous.

12. The method of claim 1, wherein the high power microwave radiation is continuous.

13. The method of claim 11, wherein the high power microwave radiation is continuous.

14. The method of claim 1, wherein the first step of irradiating the specimen further comprises facilitating a diffusion of the circulating fluid into the tissue specimen.

15. The method of claim 14, wherein the step of irradiating the specimen with the high power microwave radiation further comprises fixating the tissue specimen in the circulating fluid stream.

16. A method to fixate a tissue specimen, said method comprising the steps of:
    suspending the tissue specimen in a fixating fluid stream of a formalin based solution;
    during suspending, first irradiating the specimen with a low power microwave radiation for a first set time to facilitate a diffusion of the fixating fluid into the tissue specimen; and
    during suspending, then irradiating the specimen with a high power microwave radiation for a second set time to fixate the tissue specimen with the fixating fluid.

* * * * *